United States Patent
Saint-Martin et al.

(10) Patent No.: US 7,090,679 B2
(45) Date of Patent: Aug. 15, 2006

(54) SPINAL OSTEOSYNTHESIS ASSEMBLY COMPRISING THE HEAD OF AN ANCHORING MEMBER AND A TOOL FOR FIXING SAID HEAD

(76) Inventors: Pierre Henri Saint-Martin, 2 rue Auguste Lamire, Merignac (FR) 33700; Cécile Vienney, 208, rue Emile Combes, Bordeaux (FR) F-33000; Cédric De Coninck, 7, clos de la Fontaine, Chantebois, Cestas Gazinet (FR) F-33610

( * ) Notice: Subject to any disclaimer, the term of this patent is extended or adjusted under 35 U.S.C. 154(b) by 23 days.

(21) Appl. No.: 10/491,683

(22) PCT Filed: Oct. 4, 2002

(86) PCT No.: PCT/FR02/03391

§ 371 (c)(1),
(2), (4) Date: Apr. 2, 2004

(87) PCT Pub. No.: WO03/028566

PCT Pub. Date: Apr. 10, 2003

(65) Prior Publication Data

US 2004/0249378 A1    Dec. 9, 2004

(30) Foreign Application Priority Data

Oct. 4, 2001    (FR) .................................. 01 12754

(51) Int. Cl.
*A61B 17/58* (2006.01)
*A61F 2/00* (2006.01)

(52) U.S. Cl. ........................................................ 606/99

(58) Field of Classification Search ................. 606/60, 606/61, 72, 73, 99, 205–208, 148
See application file for complete search history.

(56) References Cited

U.S. PATENT DOCUMENTS

| | | | |
|---|---|---|---|
| 4,269,178 A * | 5/1981 | Keene | 606/61 |
| 4,271,836 A * | 6/1981 | Bacal et al. | 606/61 |
| 4,411,259 A | 10/1983 | Drummond | |
| 4,815,453 A * | 3/1989 | Cotrel | 606/61 |
| 5,020,519 A * | 6/1991 | Hayes et al. | 606/237 |
| 5,364,397 A * | 11/1994 | Hayes et al. | 606/61 |
| 5,476,510 A * | 12/1995 | Eberhardt et al. | 623/2.11 |
| 5,720,751 A | 2/1998 | Jackson | |
| 6,036,692 A | 3/2000 | Burel et al. | |
| 6,066,143 A * | 5/2000 | Lane | 606/104 |
| 6,183,472 B1 | 2/2001 | Lutz | |
| 6,224,598 B1 * | 5/2001 | Jackson | 606/61 |

(Continued)

OTHER PUBLICATIONS

European Search Report for Application No. PCT/FR 02/03391 dated Jan. 27, 2003.

*Primary Examiner*—Eduardo C. Robert
*Assistant Examiner*—Anu Ramana
(74) *Attorney, Agent, or Firm*—Lerner, David, Littenberg, Krumholz & Mentlik, LLP

(57) ABSTRACT

This invention relates to a spinal osteosynthesis assembly comprising the head of an anchoring member consisting of at least one arm and a tool for fixing said head to a spinal osteosynthesis system. The inventive assembly is characterized in that the tool can hold the head by creating at least one lateral support on at least one lateral edge of the arm and an additional support on the head in the opposite direction of the lateral support.

10 Claims, 4 Drawing Sheets

U.S. PATENT DOCUMENTS

| | | | |
|---|---|---|---|
| 6,475,218 B1 * | 11/2002 | Gournay et al. | 606/61 |
| 6,530,929 B1 * | 3/2003 | Justis et al. | 606/103 |
| 6,726,692 B1 * | 4/2004 | Bette | 606/99 |
| 6,746,449 B1 * | 6/2004 | Jones et al. | 606/61 |
| 6,872,208 B1 * | 3/2005 | McBride et al. | 606/61 |
| 2003/0216752 A1 * | 11/2003 | Williamson et al. | 606/139 |

* cited by examiner

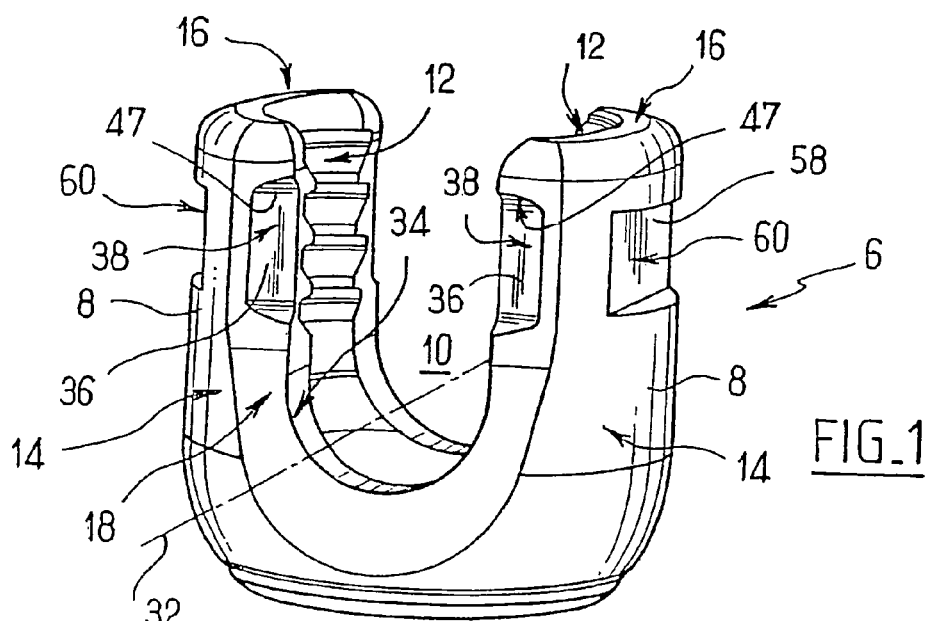
FIG.1
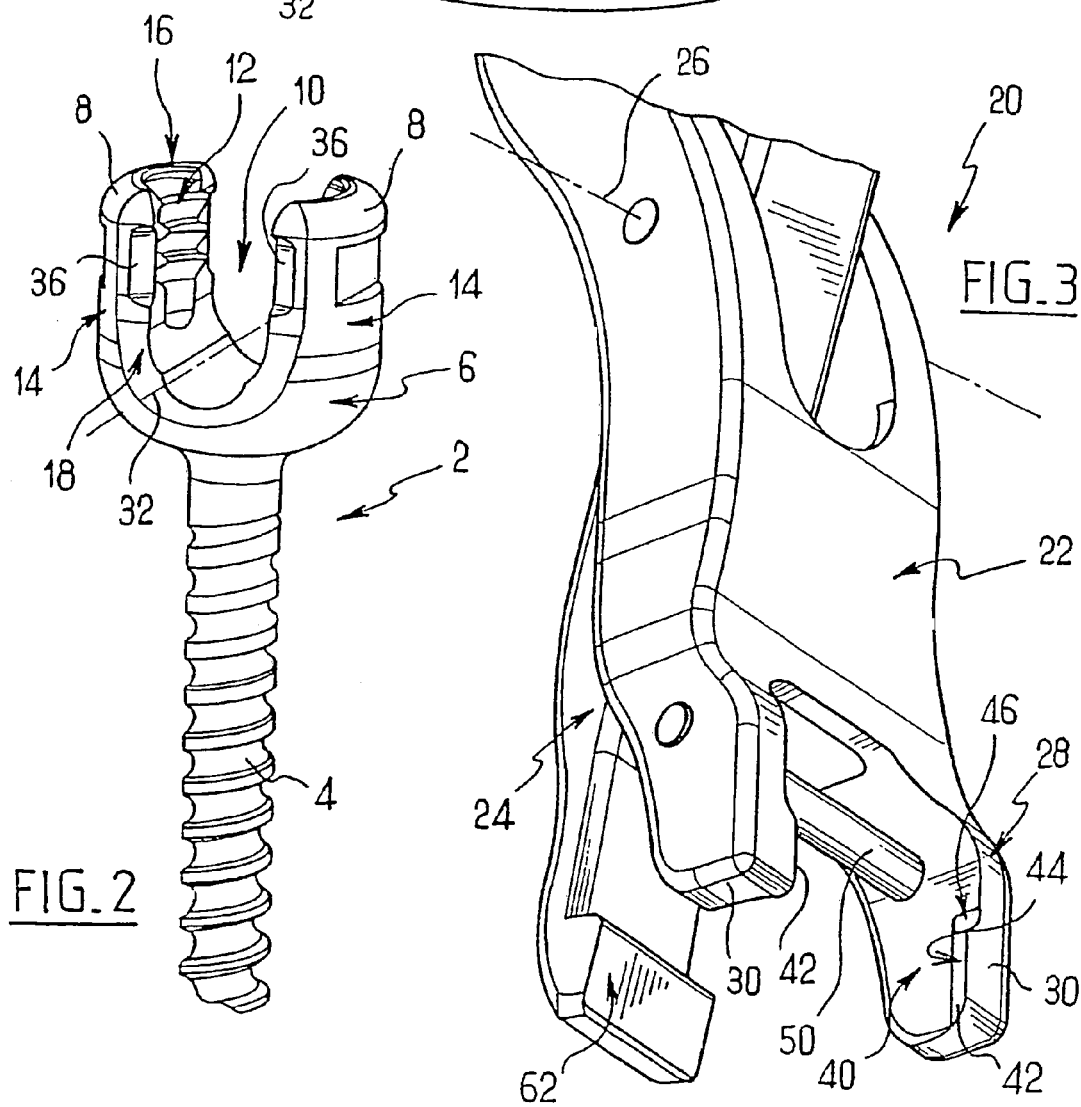
FIG.2
FIG.3

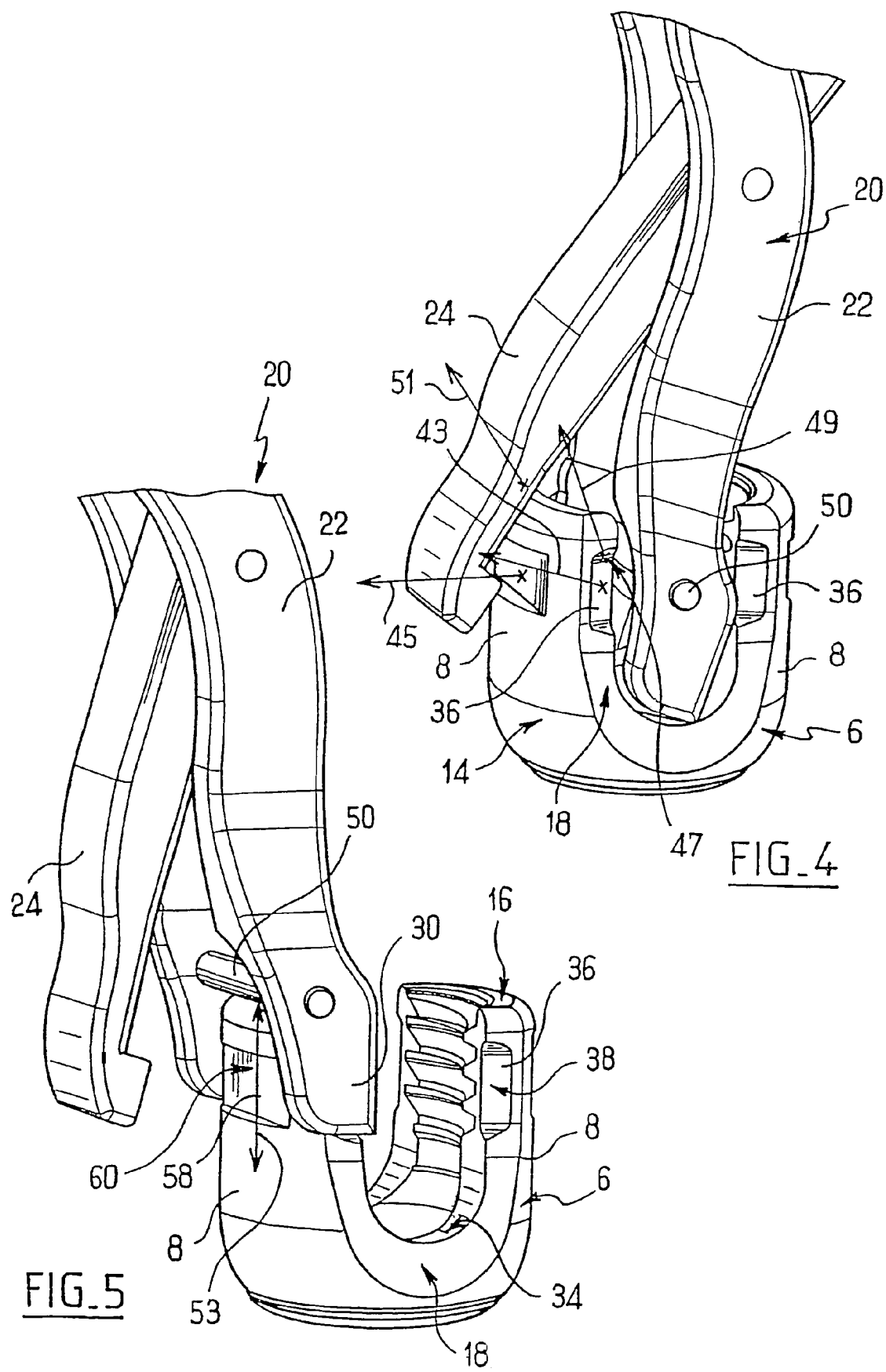
FIG_4
FIG_5

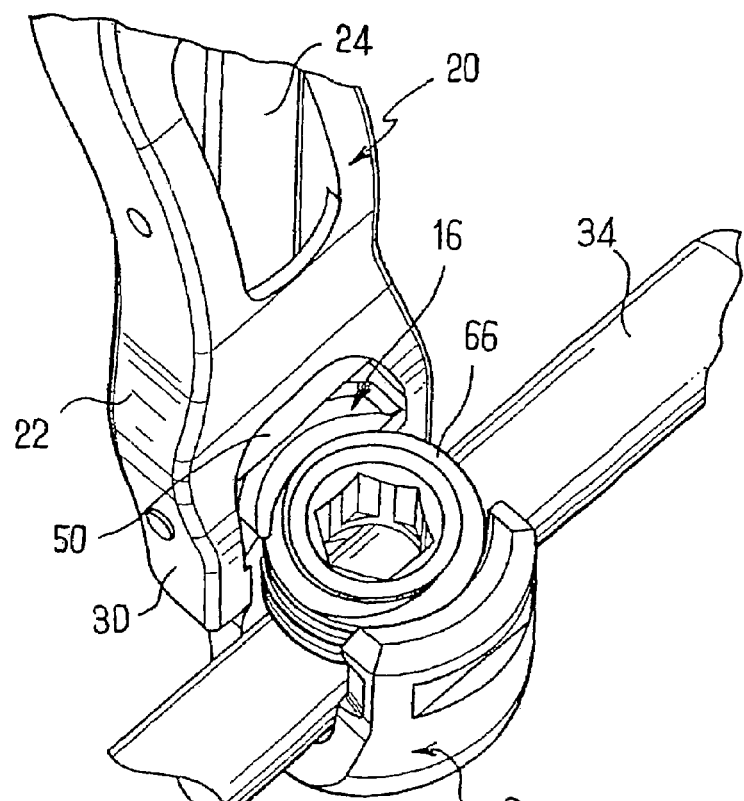
FIG_7
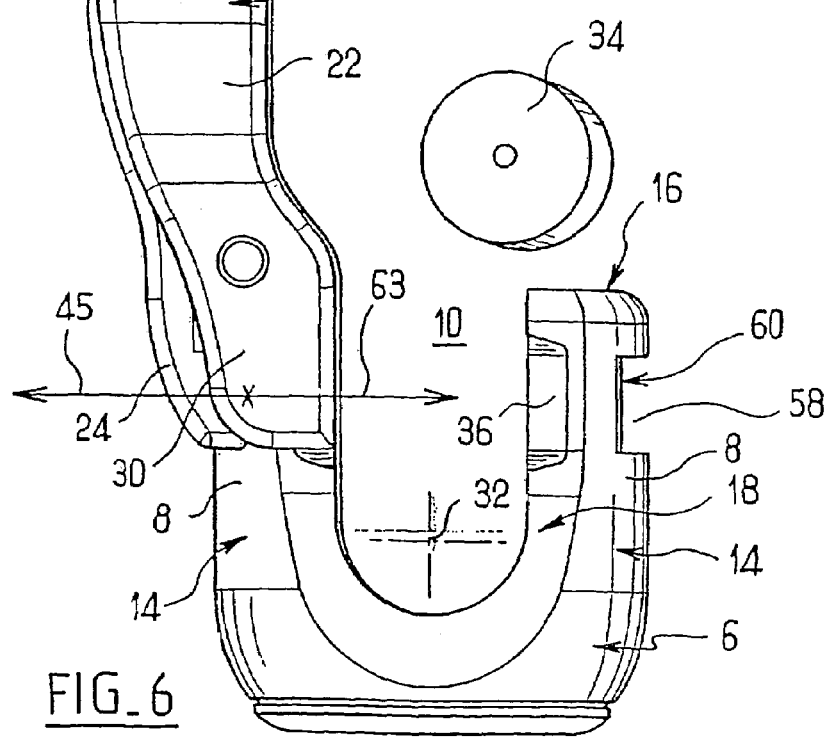
FIG_6

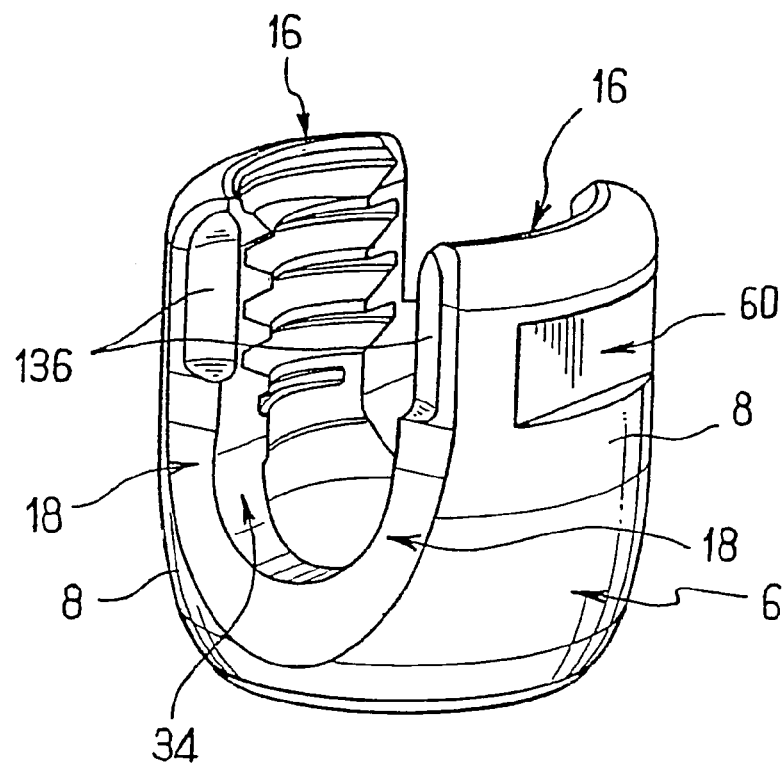
FIG_8
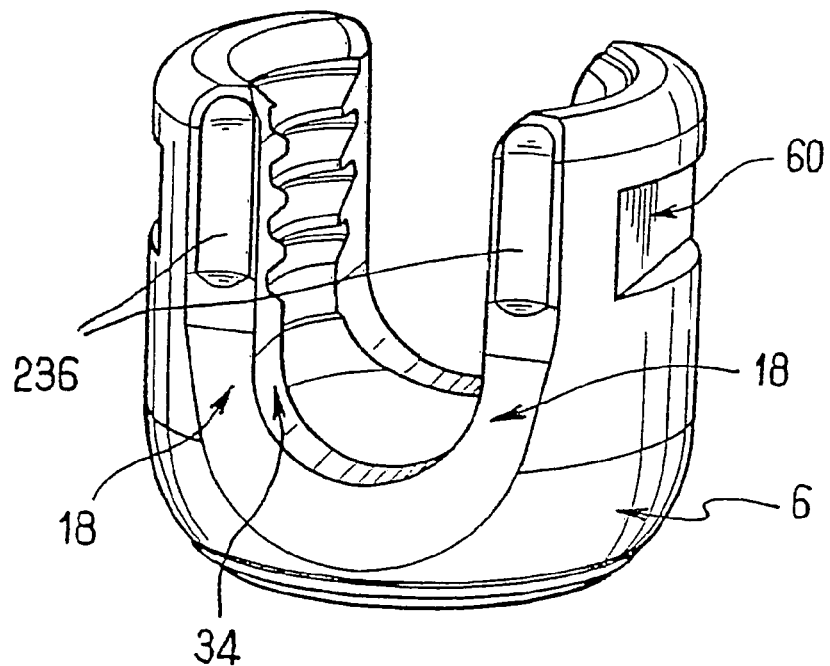
FIG_9

SPINAL OSTEOSYNTHESIS ASSEMBLY COMPRISING THE HEAD OF AN ANCHORING MEMBER AND A TOOL FOR FIXING SAID HEAD

BACKGROUND OF THE INVENTION

The invention relates to assemblies for osteosynthesis of the spine, and in particular to the tools used while fixing such assemblies.

Numerous assemblies are known for the osteosynthesis of the spine, for example the assembly disclosed in document EP-0885 598. Such assemblies generally include anchor members in the form of screws or hooks that are connected to one another by one or more link elements in the form of rods or plates. The function of such assemblies is to rectify the shape of a deformed vertebral column or to enable osteosynthesis to take place in one or more fractured vertebrae. For this purpose, the anchor members are fixed rigidly to the vertebrae.

Each such member must be placed in a very precise position. For this purpose, tools are known that enable the member to be held temporarily so as to assemble it rigidly to the other parts in a desired position. Nevertheless, most such tools do not give satisfaction, either because they do not hold the member in satisfactory manner or because their size makes it necessary to release the member in order to be able to fix it to the other elements of the assembly. In particular, such tools do not give satisfaction when it is necessary to hold an anchor member whose head includes at least one branch.

BRIEF SUMMARY OF THE INVENTION

An object of the invention is to provide a tool enabling the head of an anchor member that includes at least one branch to be held appropriately even while said member is being fixed to other parts of the assembly.

To this end, the invention provides a system for osteosynthesis of the spine, the system comprising:

a head of anchor member, the head including at least one branch; and a tool for fixing the head to an assembly for osteosynthesis of the spine, the tool being suitable for holding the head by applying lateral thrust on at least one lateral edge of the branch and by applying additional thrust on the head in the opposite direction to the lateral thrust.

Thus, the thrust of at least one of the lateral edges makes it possible to apply the additional thrust other than on the face of the branch that is to come into contact with the link element. The additional thrust may, for example, be applied to the tip of the branch or to the other face of the branch. The head can thus be assembled to other elements of the assembly while it is being held by the tool. In addition, the tool presents two or three thrust points on the head, thereby ensuring that the head is held properly by the tool.

The system of the invention may also present at least any one of the following characteristics:

the tool is suitable for applying two lateral thrusts on the respective lateral edges of the branch;

the tool comprises a one-piece arm suitable for applying the lateral thrust and the additional thrust simultaneously;

the tool and the lateral edges are shaped with complementary shapes to prevent the tool sliding upwards and/or downwards relative to the head;

the tool presents two portions in relief for applying thrust against the edges;

the lateral edges present two cavities against which the tool is suitable for applying thrust;

the cavities are open towards the tip of the head;

the additional thrust is applied to a top edge of the branch;

the contact between the tool and the top edge takes place along a line or over an area;

the tool includes an elongate element extending transversely relative to a general direction of the tool, whereby the tool is capable of applying thrust to the top edge;

the tool includes two fingers supporting the elongate element, the system being arranged in such a manner that the elongate element can be placed in a slot of the head without the fingers extending into the slot;

the fingers extend from one end of an arm of the tool;

the tool has an arm suitable for applying the additional thrust;

the additional thrust is applied against a face of the branch;

the tool and the face are shaped with complementary shapes to prevent the tool sliding upwards or downwards relative to the head;

the branch is a first branch, and the head includes a second branch extending facing the first branch;

the each lateral thrust is applied in a direction away from the second branch;

the tool is suitable for holding the branch while leaving access to a slot formed between the two branches;

the tool comprises two arms that are hinged to each other;

the system includes an anchor suitable for being anchored in the spine, the head being integral with said anchor member;

the system comprises an anchor member suitable for being anchored in the spine, the head being suitable for fixing to the anchor member in different angular positions of the head relative to the anchor member; and an assembly for osteosynthesis of the spine comprising an anchor member including a head, the head having a branch presenting at least one lateral edge, and the each edge presenting a blind cavity cut into the edge.

BRIEF DESCRIPTION OF THE DRAWINGS

Other characteristics and advantages of the invention appear further from the following description of a preferred embodiment and of variants given as non-limiting examples. In the accompanying drawings:

FIG. 1 is a perspective view of an anchor member head of a system constituting the preferred embodiment of the invention;

FIG. 2 is a view on a larger scale of the anchor member with its head, in a variant embodiment;

FIG. 3 is a fragmentary perspective view of a tool of the system constituting the preferred embodiment of the invention;

FIGS. 4 to 7 are four perspective views showing four steps in the co-operation between the tool of FIG. 3 with the head of FIG. 1 while the anchor member is being assembled with other elements of the osteosynthesis assembly; and FIGS. 8 and 9 are views analogous to FIG. 1 showing variant embodiments of the head.

DETAILED DESCRIPTION OF THE INVENTION

A preferred embodiment of the system for osteosynthesis of the spine is described below. This system comprises a tool as shown in FIG. 3 and an assembly for osteosynthesis of the spine. The assembly comprises various parts, including mutually identical anchor members of the type shown in FIGS. 1 and 2.

Each anchor member comprises a threaded shank and a head. In the embodiment of FIG. 1, the head forms a part of an anchor member of conventional polyaxial type. In such a member, the head 6 can be mounted on the shank of the body so as to occupy different angular positions relative thereto and it can be locked in a selected angular position. The head 6 has two branches 8 extending at a distance from each other and facing each other. The two branches give the head a U-shape defining between them a slot 10. Overall, the member is in the form of a tuning fork identical to the variant shown in FIG. 2. The two branches 8 are in the form of cylindrical sectors geometrically defined by a common cylinder that is coaxial with the shank 4. The two branches are symmetrical to each other about a longitudinal midplane constituting the plane of symmetry of the member. The member also presents another longitudinal midplane of symmetry perpendicular to the first.

Each branch 8 presents an inside face 12 facing the other branch and an outside face 14 facing away from the other branch. Each branch presents an essentially plane tip 16 in the form of a circular arc, and two lateral edges 18 each constituting a junction between the inside and outside faces of the branch. These characteristics of the anchor member 2 are themselves known and are not described in greater detail herein. Reference can be made in particular to European patent document No. 0 885 598.

With reference in particular to FIG. 3, the tool 20 of the system of the invention comprises two arms 22 and 24 each being of generally elongate and substantially rectilinear shape. The two arms are hinged to each other about an axis 26 perpendicular to the longitudinal direction of the arms. Along said axis 26, the arm 22 is wider than the other arm 24. The arm 22 is referred to herein as the "first" arm. The first arm 22 is in the form of a fork over a major fraction of its length extending from a proximal end of the arm (not shown) to a zone of the arm that lies between the axis 26 and the distal end 28 of the arm. This distal end 28 is also in the form of a fork, but over a length that is much shorter than the other fork. This fork thus defines two fingers 30 which together form the distal end 28. The second arm 24 passes through the larger fork of the first arm level with the axis 26.

The head 6 and the tool 22 are configured so that the tool is suitable for holding the head, and in particular in rigid manner. The means enabling it to hold the head in this way are described below.

On the head 6, each edge 18 presents a chamfer extending from the tip of the edge to a low portion of the head where it extends in continuity with the corresponding edge of the other branch. Each pair of edges thus forms a U-shape. The chamfer is oriented substantially towards the outside of the head, essentially in a direction parallel to an axis 32 along which a link rod 34 is to extend in the slot defined between the branches and as shown in FIG. 7.

The head 6 presents second chamfers 34 extending to the junction of each edge 18 with the inside faces 12 of the branches. This second chamfer 34 is also generally U-shaped. It faces essentially towards the inside of the head. In its bottom portion it is essentially in the form of a cylinder about the axis 32.

Each lateral edge 18 of each branch presents a blind cavity 36 formed both in the edge 18 and in the second chamfer 34, cutting into the ridge formed at the junction thereof. Each cavity 36 presents a plane end face 38 which constitutes the largest face of the cavity. The cavity opens out laterally relative to the edge 18 and the second chamfer 34. In contrast, it is closed upwards and downwards by residual portions of the ridge. The face 38 is parallel to the axis of the cylinder forming the branches. It slopes relative to the axis 32 and is oriented towards the outside of the head. It is oriented essentially in the opposite direction to the portion of the branch that carries it. The head 6 thus presents four cavities 36, two in each branch 8.

The fingers 30 present two plane faces 40 extending parallel to each other, facing each other, and spaced apart from each other. Each finger includes a portion in relief 42 projecting from the face 40 towards the other finger. This portion in relief is contiguous with a front edge of the finger 30. Each portion in relief 42 presents in particular a plane face 44 parallel to a longitudinal direction of the tool and oriented towards the other finger while sloping rearwards, i.e. towards the second arm 24 when the arms are in the position shown in FIG. 3 where the distal ends of the two arms are adjacent to each other.

The cavities 36 and the portions in relief 42 are shaped and positioned in such a manner that the first arm 22 can be placed relative to the head 6 so that the faces 44 and the portions in relief 42 come into contact with the faces 38 of the two cavities 36 respectively in either one of the two branches. In this position, as shown in particular in FIGS. 5, 6, and 7, each of the portions in relief 42 applies lateral thrust 43 on the associated cavity 36 in the direction opposite to the other branch (only one direction of applied thrust is shown in FIG. 4). The resultant 45 of these two applied thrusts forms thrust oriented away from the other branch.

Each portion in relief 42 also presents a top face 46 of plane shape that slopes relative to the vertical direction, forming a bevel on said portion in relief.

When the first arm 22 is thrust against the edges 18 in the manner explained above, the faces 46 of the portions in relief are thrust against the top faces 47 of the respective cavities 36. The corresponding lateral thrust 49 is likewise oriented away from the other branch, but is oriented above all in an upward direction towards the tip of the branch. In this case also, the resultant 51 of these two thrusts forms thrust oriented away from the other branch and upwards.

With reference to FIG. 3, the tool 20 includes an elongate transverse element 50 implemented in this example as a rod. The rod 50 extends parallel to the pivot axis 26 from one of the fingers 30 to the other finger across the fork that the fingers define.

The rod 50 is shaped and positioned in such a manner that when the portions in relief 42 are thrust into the cavities 36 as explained above, the rod 50 thrusts against the tip 16 of the same branch as shown in particular in FIGS. 5 and 7. The thrust 58 from the rod 50 on said tip is oriented towards the bottom of the head parallel to the longitudinal direction of the anchor member as shown in FIG. 5. Given the cylindrical shape of the outside face of the rod and the essentially plane shape of the tip 16, contact between these two elements takes place along a line. In the presence of a transverse element 50 of rectangular or square right section, this contact would take place over an area.

If the resultant thrust 51 of the thrust 49 of the faces 46 on the faces 47 of the cavities is considered as a first thrust and if the thrust 58 of the rod 50 on the tip 16 is considered as a second thrust, it can be seen that these two thrusts are oriented in opposite directions, even if these two directions are not rigorously collinear. Nevertheless, when the tool holds the head by means of these thrusts only, account needs to be taken of the action of gravity on the head. In the position of FIG. 5 it can be seen that the geometrical line formed by the two faces 46 is very close to the rod 50 while the center of gravity of the head is offset therefrom. Consequently, if it is considered that the head can be pivoted about the line formed by the two faces 46, the weight of the head tends to turn it so as to press the tip 16 against the rod 50, thus leading to a stable position for the head held by the tool. Although in this position the head is not rigidly held by the tool, it can be manipulated without difficulty by means of the tool, in particular in order to be moved.

The outside face 14 of each branch 8 presents a cavity 58 whose end wall is formed by a face 60 extending parallel to the axis 32 and to the axis of the cylinder. The face 60 is generally rectangular in shape. It opens out laterally in the outside face 14 on both sides. Nevertheless, it is closed upwards and downwards by the top and bottom edges of the cavity.

The distal end of the second branch 24 is oriented towards the distal end 28 of the first branch and is terminated by a plane face 62 of rectangular shape substantially identical to the shape of the faces 60. The face 62 extends towards the faces 44 of the portions in relief 42.

The cavities 58 and the face 62 are formed and positioned in such a manner that when the first arm 22 is thrust against either one of the branches by means of the portions in relief 42 and by means of the rod 50, as explained above, then the second arm 24 can be driven so as to cause its distal end to penetrate into the cavity 58 of the same branch, thus thrusting the face 62 against the face 60. The thrust 63 of the second arm on the branch, as shown in FIG. 6, is thus oriented towards the other branch in a direction opposite from the thrust 45 delivered by the first arm by means of the portions in relief 42. This time, if the two thrusts 43 imparted by the portions in relief 42 in the cavities 36 are considered as constituting a first thrust 45 and the thrust imparted by the face 62 in the cavity 60 is considered as constituting a second thrust 63, it can be seen that these two thrusts are oriented in opposite directions and deliver a kind of pinching effect on the branch by means of the tool. This pinching enables the operator to hold the head rigidly by means of the tool. For this purpose, the cavities 58 are preferably at the same height as the cavities 36. Retention is made stronger by the operator clamping the two proximal ends of the arms towards each other. This rigid retention of the head by means of the tool takes place via only one of the two branches of the head. This can be done via either one of the two branches.

It should also be observed that retention of the head in the tool solely by means of the portions in relief 42 and the rod 50 likewise takes place via the first arm 22 on its own.

The configuration of the end of the first arm 22 is such that the rod 50 can be placed in the slot 10 as shown in FIG. 4 without the fingers 30 extending into the slot. In this situation, the fingers then extend vertically relative to the edges 18. When the head is supported movably on the shank of the member, this position of the tool within the head enables the head to be turned about its own axis by pressing the rod against the branches. Similarly, when the head is integral with the shank, this position enables the member to be turned about its longitudinal axis.

FIGS. 4 to 6 show various different relative positions of the head and the tool that can appear during surgery to install the osteosynthesis assembly.

As described above, FIG. 4 shows the disposition of the rod in the slot 10 of the head which makes it possible, by turning the tool about its own longitudinal axis, to cause the head of the member to turn about its own axis until it reaches a desired position.

FIG. 5 shows the head being held by means of the first arm 22 on its own via the portions in relief 42 and the rod 50. The second arm 24 is then at a distance from the head. In practice, it is possible to go directly from the position of FIG. 4 to the position of FIG. 5.

It will be observed that in the position of FIG. 4, the distal end 28 of the first arm 22 automatically centers the tool relative to the head prior to passing into the position of FIG. 5.

Thereafter, by bringing the distal end of the second arm 24 against the branch that is already held, the head can be held rigidly by the tool as shown in FIG. 6. The head can then be held firmly.

It will be observed that the tool leaves the slot 10 between the branches completely free, and also the access thereto free so as to make it possible to install a link member such as a rod 34 in the slot.

With reference to FIG. 7, the following step could be installing a locking element 66. In this case the locking element is in the form of a ring having an outside thread for co-operating with a thread formed in the inside face 12 of the branches so that the ring can clamp the rod 34 against the bottom of the slot 10. The arrangement of the anchor member, the rod, and the ring is conventional. The ring presents a hexagonal socket in its center for tightening purposes. The tool allows the head to be held in position possibly until after the ring has been tightened and the anchor member has been locked completely relative to the rod. The operator can then release the hold of the tool on the head. It will naturally be understood that the tool is not intended to remain on the assembly after surgery, since the tool does not form part of the osteosynthesis assembly proper.

The tool in this embodiment of the invention thus enables the head to be held in two different ways, firstly by means of the arm 22 on its own and secondly rigidly by means of both arms. As can be seen, in each position for holding the head in the tool, contact takes place via at least three points.

FIG. 8 shows a variant embodiment of this invention. In this variant, the system is identical to that described above except that the cavities 136 formed in the edges 18 of the head are upwardly open towards the tips of the branches. It follows that the distal end of the first arm 22 can be separated from the branch by sliding upwards. In contrast, the head can no longer be held on the first arm 22 by means of the rod 50 without also making use of the second arm 24.

Another variant embodiment is shown in FIG. 9. In this embodiment, the end faces of the cavities 236 are cylindrical in shape, with the axes of the cylinders being parallel to the longitudinal direction of the anchor member. Again the cavities are upwardly open.

When the head is integral with the shank as in the variant of the anchor member shown in FIG. 2, the chamfer 34 can be omitted.

Naturally, numerous modifications can be applied to the invention without going beyond the ambit thereof.

While the head is being held rigidly by the branch being pinched between the two arms, provision can be made for the first arm 22 to apply lateral thrust 43 or 49 in only one cavity 36, providing the cavity and the face 58 are suitably configured to ensure that the two applied thrusts are in substantially opposite directions. For example the faces 60, 62 could be given a shape that is not plane (e.g. spherical) so that they assemble together with male/female interfitting.

A tool could be provided that has a transverse element 50 independently of the other characteristics of the invention.

The invention claimed is:

1. A tool for holding an anchor member for use in osteosynthesis of the spine, said anchor member having a head portion with two branch portions separated from one another by a slot, each branch portion having a top and two edges each having a contact portion, said tool comprising a first arm member having a distal end with two finger members spaced apart from each other and a transverse member arranged so as to extend between the two finger members, each finger member having a contact portion which is arranged such that the contact portion of one of the finger members is spaced apart from the contact portion of the other of the finger members a first distance which is substantially the same as that between the contact portions of the edges of one of the branch portions, wherein the tool is operable to engage said anchor member such that the transverse member contacts the top of only one of the branch portions while the contact portions of the finger members contact the corresponding contact portions of the edges of only the one respective branch portion so as to enable manipulation of said anchor member by the tool.

2. The tool according to claim 1, wherein the transverse member is a rod.

3. The tool according to claim 1, wherein each said branch portion further has an outside face which includes a contact portion, and wherein the tool further comprises a second arm member pivotally coupled to the first arm member and having a distal end with a face portion, in which the face portion of the second arm member is operable to contact the contact portion of the outside face of the respective branch portion when the tool engages said anchor member.

4. The tool according to claim 3, wherein the contact portion of the outside face of each said branch portion includes a cavity, and wherein the face portion of the second arm member is configured so as to fit within said cavity when the face portion contacts the contact portion of the outside face of the respective branch portion.

5. The tool according to claim 1, wherein said transverse member is further arranged so as to be spaced apart along a predetermined direction from the contact portions of the finger members a second distance which is substantially the same as the distance between the top and the contact portions of the two edges of the respective branch portion along said predetermined direction.

6. A system for use in osteosynthesis of the spine, said system comprising:
 an anchor member having a head portion with two branch portions separated from one another by a slot, each branch portion having a top, two edges each having a corresponding contact portion, and an outside face having a contact portion; and
 a tool including a first arm member and a second arm member pivotally coupled to the first arm member, said first arm member having a distal end with two finger members spaced apart from each other and a transverse member arranged so as to extend between the two finger members, each finger member having a contact portion which is arranged such that the contact portion of one of the finger members is spaced apart from the contact portion of the other of the finger members a distance which is substantially the same as that between the contact portions of the edges of one of the branch portions, said second arm member having a distal end with a face portion,
 wherein the tool is operable to securely hold said anchor member by having (i) the transverse member of the first arm member contact the top of only one of the branch portions, (ii) the contact portions of the finger members of the first arm member contact the contact portions of the edges of only the one respective branch portion, and (iii) the face portion of the second arm member contacts the contact portion of the outside face of only the one respective branch portion.

7. The system according to claim 6, wherein the transverse member is a rod.

8. The system according to claim 6, wherein the contact portion of the outside face of each said branch portion includes a cavity, and wherein the face portion of the second arm member is configured so as to engage the cavity when the tool is operated.

9. The system according to claim 8, wherein the cavity includes a flat wall having a generally rectangular shape, and wherein the face portion of the second arm member has a generally rectangular shape which is similar in size to that of the flat wall.

10. The tool according to claim 6, wherein said transverse member is further arranged so as to be spaced apart along a predetermined direction from the contact portions of the finger members a second distance which is substantially the same as the distance between the top and the contact portions of the two edges of the respective branch portion along said predetermined direction.

* * * * *